United States Patent [19]
Kinzler et al.

[11] Patent Number: 6,048,701
[45] Date of Patent: Apr. 11, 2000

[54] ANTIBODY DETECTION OF MISMATCH REPAIR PROTEINS

[75] Inventors: Kenneth W. Kinzler, BelAir; Bert Vogelstein, Baltimore, both of Md.; Marilee Burrell, Cambridge; David E. Hill, Arlington, both of Mass.; Fredrick S. Leach, Dallas, Tex.

[73] Assignee: The Johns Hopkins University, Baltimore, Md.

[21] Appl. No.: 08/709,784

[22] Filed: Sep. 9, 1996

Related U.S. Application Data

[63] Continuation of application No. 08/480,351, Jun. 7, 1995, abandoned.
[51] Int. Cl.$^7$ .................................................. G01N 33/53
[52] U.S. Cl. .................... 435/7.1; 530/387.1; 530/350
[58] Field of Search ................ 435/7.23; 530/387.1, 530/350

[56] References Cited

U.S. PATENT DOCUMENTS

| | | | |
|---|---|---|---|
| 4,666,828 | 5/1987 | Gusella ........................................ | 435/6 |
| 5,075,217 | 12/1991 | Weber .......................................... | 435/6 |
| 5,098,823 | 3/1992 | Bodmer et al. ............................. | 435/6 |

FOREIGN PATENT DOCUMENTS

| | | |
|---|---|---|
| 9514085 | 5/1995 | WIPO . |

OTHER PUBLICATIONS

S.N. Thibodeau, et al., Microsatellite Instability in Cancer of the Proximal Colon, Science, vol. 260, May 7, 1993, 816–819.

Richard Fishel, et al., The Human Mutator Gene Homolog MS H2 and Its Association with Hereditary Nonpolyposis Colon Cancer, Cell, vol. 75, 1027–1038, Dec. 3, 1993.

Leach, et al., "Mutations of a mutS Homolog in Hereditary Nonpolyposis Colorectal Cancer," *Cell,* 75:1215–1225, 1993.

Parsons, et al., "Hypermutability and Mismatch Repair Deficiency in RER$^+$Tumor Cells", *Cell,* 75:1227–1236 (1993).

Wilson, TM. et al. 1995—Cancer Res. 55: 5146–5250.

Lim, PC. et al. 1996. Clin. Cancer Res. 2: 1907–1911.

Monell, CR. et al. 1995. Proc. Amer. Assoc. Cancer Res. 36(0), p. 558.

Nicolaides, NC. et al. 1994. Nature, 371: 75–80.

Inokuchi, K. et al. 1995. Biochem. Biophys. Res. Comm. 214(1): 171–9.

Vani RG. et al. 1997—Gene 185(A): 19–26.

*Primary Examiner*—Paula K. Hutzell
*Assistant Examiner*—Minh-Tam Davis
*Attorney, Agent, or Firm*—Banner & Witcoff, Ltd.

[57] ABSTRACT

Antibodies directed to human protein mismatch repair proteins can be used diagnostically to discriminate between proliferating and non-proliferating cells. In addition, they can be used to determine whether cells have a mismatch repair defect caused by a mutation in e.g., hMSH2, hMLH1, or hPMS2. They can also be used to monitor the efficacy of anti-neoplastic therapies.

30 Claims, 3 Drawing Sheets

(1 of 3 Drawing Sheet(s) Filed in Color)

ANTIBODY DETECTION OF MISMATCH REPAIR PROTEINS

This application is a continuation of Ser. No. 08/480,351 filed Jun. 7, 1995 now abandoned.

BACKGROUND OF THE INVENTION

HNPCC (Lynch syndrome) is one of the most common cancer predisposition syndromes, affecting as many as 1 in 200 individuals in the western world (Lynch et al., 1993). Affected individuals develop tumors of the colon, endometrium, ovary and other organs, often before 50 years of age. Although the familial nature of this syndrome was discovered nearly a century ago (Wartin et al., 1913), the role of heredity in its causation remained difficult to define (Lynch et al., 1966). Recently, however, linkage analysis in two large kindreds demonstrated association with polymorphic markers on chromosome 2 (Peltomaki et al., 1993a). Studies in other families suggested that neoplasia in a major fraction of HNPCC kindreds is linked to this same chromosome 2p locus (Aaltonen et al., 1993).

HNPCC is defined clinically by the occurrence of early-onset colon and other specific cancers in first degree relatives spanning at least two generations (Lynch et al., 1993). The predisposition is inherited in an autosomal dominant fashion. It was initially expected that the gene(s) responsible for HNPCC would be a tumor suppressor gene, as other previously characterized cancer predisposition syndromes with this mode of inheritance are caused by suppressor gene mutations (reviewed in Knudson, 1993). But the analysis of tumors from HNPCC patients suggested a different mechanism. Most loci encoding tumor suppressor genes undergo somatic losses during tumorigenesis (Stanbridge, 1990). In contrast, both alleles of chromosome 2p loci were found to be retained in HNPCC tumors (Aaltonen et al., 1993). During this search for chromosome 2 losses, however, it was noted that HNPCC tumors exhibited somatic alterations of numerous microsatellite sequences.

Widespread, subtle alterations of the cancer cell genome were first detected in a subset of sporadic colorectal tumors using the arbitrarily-primed polymerase chain reaction (Peinado et al., 1992). These alterations were subsequently found to represent deletions of up to 4 nucleotides in genomic polyA tracts (Ionov et al., 1993). Other studies showed that a similar, distinctive subgroup of sporadic tumors had insertions or deletions in a variety of simple repeated sequences, particularly microsatellite sequences consisting of dinucleotide or trinucleotide repeats (Ionov et al., 1993; Thibodeau et al., 1993; Aaltonen et al., 1993). Interestingly, these sporadic tumors had certain features in common with those developing in HNPCC kindreds, such as a tendency to be located on the right side of the colon and to be near-diploid. These and other data suggested that HNPCC and a subset of sporadic tumors were associated with a heritable defect causing replication errors (RER) of microsatellites (Ionov et al., 1993; Aaltonen et al., 1993).

The mechanism underlying the postulated defect could not be determined from the study of tumor DNA, but studies in simpler organisms provided an intriguing possibility (Levinson and Gutman, 1987; Strand et al., 1993). This work showed that bacteria and yeast containing defective mismatch repair genes manifest instability of dinucleotide repeats. The disruption of genes primarily involved in DNA replication or recombination had no apparent effect on the fidelity of microsatellite replication (reviewed in Kunkel, 1993). These pivotal studies suggested that defective mismatch repair might be responsible for the microsatellite alterations in the tumors from HNPCC patients (Strand et al., 1993). This hypothesis was proven when hMSH2, one of the genes responsible for HNPCC, was identified. Leach et al., (1993); Fishel, et al., (1993).

There is a need in the art for methods of diagnosing and prognosing mismatch repair defects involved in inherited and somatic cancers. Such tumors have a more favorable prognosis than others. There is also a need in the art for improved methods for assessing the proliferative index of cells which index can be used as a prognostic factor in cancers.

SUMMARY OF THE INVENTION

It is an object of the invention to provide a method of discriminating proliferating from non-proliferating cells in a tissue.

It is another object of the invention to provide a method for determining a mismatch repair defect, such as in hMSH2, hMLH1, or hPMS2 genes in tumor cells.

It is yet another object of the invention to provide a method of monitoring the effectiveness of anti cancer therapy in neoplastic tissue.

It is still another object of the invention to provide methods for discriminating between proliferating and non-proliferating cells.

It is an object of the invention to provide a method of identifying tumor-bearing individuals.

These and other objects of the invention are provided by one or more of the embodiments shown below. In one embodiment of the invention a method is provided of discriminating proliferating from non-proliferating cells in a tissue. The method comprises the steps of: contacting a tissue comprising cells with antibodies specifically immunoreactive with a mismatch repair protein, to form antibody-antigen complexes; and determining the presence of said antibody-antigen complexes in said cells, said presence indicating proliferating cells.

In another embodiment of the invention a method is provided for determining a mismatch repair defect in a mismatch repair gene, such as hMSH2, hMLH1, or hPMS2, in tumor cells, comprising the steps of: contacting a tissue comprising cells with antibodies specifically immunoreactive with a mismatch repair protein to form antibody-antigen complexes; and determining nuclear or non-nuclear localization of said antibody-antigen complexes, lack of nuclear staining indicating a defect in a mismatch repair gene.

In yet another embodiment of the invention, a method is provided for monitoring the effectiveness of anti-cancer therapy in neoplastic tissue. The method comprises the steps of: contacting a sample of a neoplastic tissue which has been subjected to an anti-cancer therapy with antibodies specifically immunoreactive with a mismatch repair protein to form antibody-antigen complexes; determining the amount of said antibody-antigen complexes in said sample; and comparing the amount of antibody-antigen complexes in said sample with an amount determined at an earlier time, a reduction in the amount of antibody-antigen complexes indicating effective therapy.

According to yet another embodiment of the invention, a method is provided for discriminating proliferating from non-proliferating cells. The method comprises the steps of: preparing a lysate of cells to be tested; contacting said lysate with antibodies specifically immunoreactive with a mismatch repair protein to form antibody-antigen complexes;

and determining the amount of antibody-antigen complexes formed in said lysate, a lysate of test cells which provides more antibody-antigen complexes than control lysates of non-tumor cells indicating that the test cells are proliferating.

In still another embodiment of the invention, a method is provided for discriminating proliferating from non-proliferating cells. The method comprises the steps of: isolating nuclei of cells to be tested; preparing a lysate of said nuclei of said cells to be tested; contacting said lysate with antibodies specifically immunoreactive with a mismatch repair protein to form antibody-antigen complexes; and determining the amount of antibody-antigen complexes formed in said lysate, a lysate of nuclei which provides more antibody-antigen complexes than control lysates of non-tumor cell nuclei indiating that the test cells are proliferating.

According to yet another embodiment of the invention, a method is provided for identifying tumor-bearing individuals. The method comprises the step of: detecting auto-antibodies to a mismatch repair protein in a human, wherein presence of said auto-antibodies indicates the presence of a tumor in the human. The invention thus provides the art with immunological assays which can provide diagnostic and prognostic information to improve the assessment of cancers and the evaluation of treatment options.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 1 shows that both antibodies immunoprecipitate a 100 kDa protein from HCT116 cells, which express wild type MSH2. The protein is not seen in LoVo cells. In addition, a 160 kDa protein is also detected as part of a co-precipitating complex, but only in the HCT116 cells. NMS is normal mouse serum used as a negative control.

FIG. 2 shows a comparison of three cell lines by immunoblot. SW480 cells express only wild type MSH2. LoVo cells do not express any MSH2 due to homozygous loss of both alleles. The cell line KK expresses both a full length wild type MSH2 and a smaller form, due to an in-frame deletion of 50 amino acids. Identification of the shortened form of MSH2 is indicative of the presence of mutation in the MSH2 gene.

FIG. 3A shows detection of MSH2 in paraffin-embedded tissue with EH12 while FIG. 3B shows detection of MSH2 in frozen tissue with FE11. In both cases, staining is nuclear and is predominantly localized to the lower portion of crypts which is associated with the proliferating compartment of the colonic epithelium.

DETAILED DESCRIPTION OF THE PREFERRED EMBODIMENTS

The MSH2 gene is one of at least four genes encoding proteins involved in the repair of mismatched nucleotides following DNA replication or repair. Mutations in the MSH2 gene contribute to the development of sporadic colorectal carcinoma, while germline MSH2 mutations are responsible for approximately 50% of inherited, non-polyposis colorectal carcinoma (HNPCC). Since MSH2 is ubiquitously expressed, development of other cancers besides colorectal carcinoma are also susceptible to alterations in MSH2. Studies of HNPCC families have shown that MSH2 mutations can be internal, in-frame deletions or chain-terminating mutations.

To characterize both wild-type and mutant MSH2 proteins, we have generated a series of monoclonal antibodies specifically immunoreactive with the human MSH2 protein (hMSH2). The antibodies do not immunoreact with other human proteins. Western blotting with the monoclonal antibodies demonstrates that normal cells and some colorectal tumor lines (i.e., SW480) express wild-type, full-length, 100 kDa MSH2 protein, whereas a cell line derived from an HNPCC patient carrying an in-frame deletion in one allele of MSH2 expresses both a full-length and, at low level, a shorter form. Other colorectal cancer cell lines are devoid of MSH2 protein due to either homozygous loss of MSH2 (LoVo cells, for example), instability of aberrant MSH2 protein expressed from mutant alleles, or mutations in other HNPCC genes that result in premature degradation of wild type MSH2 protein. Thus such antibodies can be used to detect loss of wild-type MSH2 proteins.

A number of surprising properties of the antibodies have been discovered. First, the MSH2 protein is expressed strongly in proliferating but not in non-proliferating cells. Second, the cellular localization of MSH2 protein is dependent upon the mismatch repair status of the cell. Mutations in any of the mismatch repair genes, including but not limited to the hMSH2, hMLH1, and hPMS2 genes causes the MSH2 protein to be aberrantly localized extra-nuclearly. If a cell is wild-type for the mismatch repair genes, the protein is mainly nuclear. Similarly other mismatch repair proteins are aberrantly localized when any one is mutated.

The ability to score a proliferative index of cells on the basis of antibody binding, rather than using radiolabeled deoxyribonucleotides, provides major practical, cost, and safety advantages. It also allows for monitoring of anti-cancer therapies on the basis of the proliferative index of the cells being treated without use of radionuclides. Successful treatment will lower the proliferative index of cancer cells. Detection of a failure to lower the proliferative index or to lower it sufficiently will allow other doses or regimens to be tried, or other anti-neoplastic agents to be used.

Proliferation can be assessed using standard immunological methods, including, but not limited to immunohistochemistry, immunofluorescence, and fluorescence activating cell sorting. In addition, lysates of cells can be prepared and tested directly to determine the amount of a mismatch repair protein expressed. Similarly, nuclei of cells can be isolated and lysed, and the lysate can be assayed for mismatch repair protein expression, typically through the use of antibodies. With lysates, enzyme linked immunosorbent assays can be used conveniently.

The observation that MSH2 is more heavily expressed in highly proliferative cancer cells than in normal cells may account for the expression of auto-antibodies to a mismatch repair protein in some cancer patients during the course of their disease. The detection of auto-antibodies to a mismatch repair protein in human subjects can be used diagnostically as an indication of the presence of a tumor in the body.

Proliferating cells can be discriminated from non-proliferating cells in a tissue using the antibodies disclosed herein. Antibodies are contacted with a tissue. Immune complexes of antibody and antigen are detected using, for example, immunohistochemistry or immunofluorescence or fluorescence activated cell sorting. The presence of immune complexes comprising the antibodies in the cells being tested indicates a proliferative state for those cells. Immunohistochemistry performed using antibodies to specifically detect MSH2 has shown that proliferating cells that express wild-type MSH2 protein are readily detected whereas non-proliferating cells are not detected. The ability to correlate cell proliferation with mismatch repair protein expression provides a means of assessing the proliferative state of a tissue simply by examining cells for mismatch repair protein expression by immunological methods. Any cell expressing only wild type forms of MSH2, MLH1, and PMS2 genes and undergoing proliferation will be detected by immunodetection methods using anti-mismatch repair protein monoclonal and/or polyclonal antibodies. Non-proliferating cells will not be detected due to lack of nuclear-localized mismatch repair protein. The overall degree of proliferation of cells in a tissue is positively correlated with the level of mismatch repair protein detected. Highly proliferative cells show high levels of nuclear localized a mismatch repair protein by immunohistochemistry or by flow cytometry or by immunofluorescence, whereas cells growing more slowly have reduced levels of mismatch repair protein.

Normal cells can be used as controls, either from matched tissues of the individual being tested in the case of immunohistochemistry, or from other normal individuals. Often it will be desirable to test a population of normal individuals to determine a range of normal values of expression of a mismatch repair protein. Typically values which are more than two standard deviations outside of the mean of the normals are considered aberrant. The setting of the range of normals versus aberrants is a matter of routine experimentation familiar to those of skill in the art.

Mismatch repair defects due to mutations in genes such as hMSH2, hMLH1, or hPMS2, in tumor cells can be determined readily using antibodies according to the present invention. Cancer cells that do not have mutations in MSH2, MLH1, or PMS2 allow detection of MSH2 whereas cancer cells with a mutation in any of the mismatch repair genes do not exhibit a wild-type pattern of mismatch repair protein expression as determined by immunohistochemical methods. Wild-type pattern of expression is nuclear, whereas mutations in the mismatch repair genes lead to loss of nuclear expression and staining. Furthermore, since alterations in the MSH2, MLH1, or PMS2 genes lead to altered mismatch repair protein expression, one can determine whether a cell line has defective DNA repair functions as demonstrated by aberrant mismatch repair protein detection in immunohistochemistry. Quantitation of mismatch repair protein can also be performed by enzyme linked immunosorbent assay (ELISA) in which mismatch repair protein is captured with one set of antibodies and then detected and quantitated with a second set of antibodies. The second set of antibodies can be directed against the mismatch repair protein or against proteins that form stable complexes in vivo with the mismatch repair protein. Alternatively, detection of captured mismatch repair protein can be performed by measuring the ability of a DNA segment containing appropriate mismatched nucleotides to be stably bound by the mismatch repair protein.

Immunoprecipitation of MSH2 protein with anti-MSH2 protein antibodies has been found to co-precipitate one or more additional proteins from lysates of normal cells but not cancer cells that are null for MSH2. Such proteins may be accessory proteins involved in mismatch repair. One such protein has an apparent molecular weight of 160 kDa.

The methods of the present invention rely on polyclonal or monoclonal antibodies that are highly specific for human mismatch repair proteins which are used according to defined protocols. We achieved specificity by first, immunizing mice with a recombinant form of MSH2 expressed in *E. coli* and purified to homogeneity by electroelution form SDS/PAGE. After a series of immunizations, mouse sera was checked for anti-MSH2 reactivity by: (1) ELISA using microtitre plates coated with GST-MSH2 antigen for positive reactivity; (2) western blotting using HCT116 or SW480 cells to detect the p100 MSH2 protein; and (3) western blotting using LoVo cells in which no p100 MSH2 is expected. After fusion of hyperimmunized mouse spleen cells to SP2/O cells, all resulting hybridomas were screened by ELISA using GST-MSH2 fusion proteins. MSH2-reactive hybridomas were subcloned twice by limiting dilution and rescreened by ELISA. Resulting stable clones were then tested by western blotting and specificity of a given monoclonal antibody was determined by comparing the signals generated from known positive and negative controls. This could be done using induced versus uninduced cell lines in which an exogenously added agent is used to turn on expression of the desired gene product. An antibody specific for the antigen of interest would detect the antigen only in lysates from the induced cells and no other proteins and not detect any proteins in the uninduced lysates. Alternatively, in cases where the genetic status is known, cells carrying a wild-type allele are compared to cells that are null for the gene in question. With MSH2, HCT116 cells are known to have a wild-type MSH2 allele and express MSH2 mRNA whereas LoVo cells have a homozygous deletion of MSH2. By either western blotting or immunoprecipitation, the 100 kDa MSH2 protein is detected only in HCT116 cells and no 100 kDa protein is seen in LoVo cells. In some cases, multiple non-specific bands will be seen depending on various conditions such as impure primary antibody, non-specific secondary antibody, extended exposure times when using chemiluminescence, poor sample preparation or handling. See the following references regarding immunological methods: WO 94/21814, Smith, K. et al., The APC Gene Product in Normal and Tumor Cells. Proc. Natl. Acad. Sci., USA 90: 2846–2850, 1993, or the manual by Harlow and Lane.

EXAMPLES

To characterize both wild type and mutant MSH2 proteins, we have generated a series of monoclonal antibodies to the human MSH2 protein.

1) Antigen and Immunizations

The antigens used to immunize mice were bacterial expressed, purified glutathione-S-transferase-MSH2 (GST-MSH2) fusion proteins. The GST-MSH2-NH fusion protein contains the 300 extreme amino-terminal MSH2 amino acids. The GST-MSH2-COOH fusion protein contains the 300 extreme carboxy-terminal MSH2 amino acids. Each was purified by separating the inclusion bodies containing the fusion proteins, by SDS-polyacrylamide gel electrophoresis. The band corresponding to the correct molecular weight was then cut out of the gel and the protein electroeluted out of the gel slice. One group of mice was immunized with the purified GST-MSH2-NH fusion protein and a second group of mice was immunized with the purified GST-MSH2-COOH fusion protein. Each of the purified fusion proteins were mixed with RIBI adjuvant prior to immunizations.

2) Fusions and Screening

One mouse which had been injected with carboxy-terminal fusion protein was sacrificed and its spleen cells fused to SP2/O cells. The resulting hybridomas were screened by ELISA on purified GST-MSH2-COOH-coated microtiter plates. Positive wells were further screened by western blot for specificity to a 100 kD protein present in HCT-116 lysates but not in LoVo lysates. Western blot-positive hybridomas were single cell subcloned twice and then put into mice for ascites production. The hybridomas FE11 and EH12 resulted from this fusion.

A second mouse, one that had been immunized with the amino terminal GST-MSH2 fusion protein, was sacrificed and its spleen cells fused to SP2/Os. Hybridomas were screened and subcloned as above, except that the initial ELISA was performed using GST-MSH2-NH-coated microtitre plates to identify hybridomas expressing antibodies reactive to the amino-terminal portion of MSH2 protein. Hybridoma GB12 resulted from this fusion.

3) Characterization of Antibodies by Western Blot and Immunoprecipitation and Immunohistochemistry FE11, EH12 and GB12 all recognize the 100 kD MSH2 protein in HCT-116 lysates by western blot and immunoprecipitation. No 100 kD protein is detected by western blot or immunoprecipitated in LoVo lysates which are null for MSH2. In addition, EH12 produces nuclear staining in formalin-fixed, paraffin-embedded, normal colon sections, localized in the proliferating cells at the base of the crypts of Lieberkuhn. FE11 stains frozen tissue sections.

The MSH2 gene encodes a protein of 934 amino acids. Normal cells and some colorectal tumor lines (i.e., SW480) express wild-type, full-length 100 kDa MSH2 protein whereas a cell line derived from an HNPCC patient (KK) carrying an in-frame deletion in one allele of MSH2 expresses both a full length and, at low level, a shorter species corresponding to the size expected for the 880 amino acid form. The LoVo colorectal line is devoid of MSH2 protein due to homozygous loss of MSH2. Many of the mutations in the MSH2 gene are truncating ones; that is, they introduce small deletions or base changes that result in expression of a shortened form of the 100 kDa wild-type MSH2 protein.

All anti-MSH2 mAbs were also evaluated for the ability to detect MSH2 protein by immunohistochemical methods. MSH2 protein is ordinarily localized to the nucleus. FE11 and EH12 detect nuclear-localized MSH2 in frozen sections or in tissue culture cells immobilized and fixed in microtitre wells and EH12 can be used to detect MSH2 protein in formalin-fixed, paraffin-embedded tissue.

Figure 1:
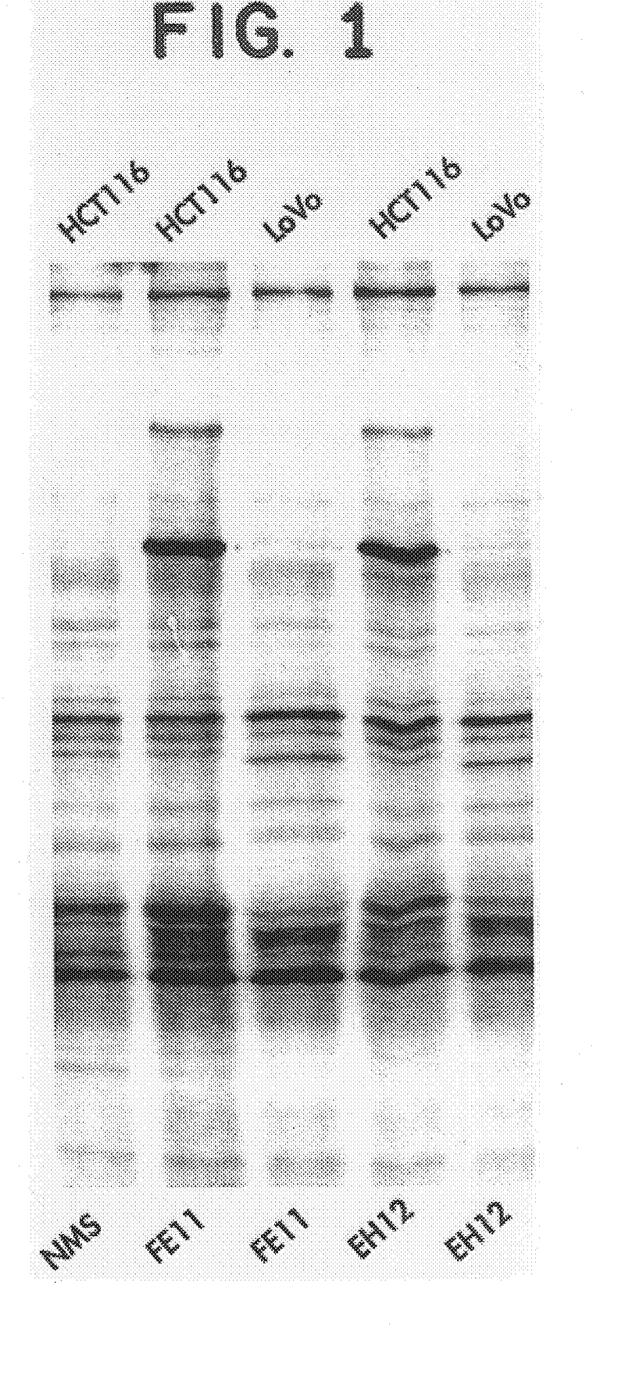
FIG. 1 is a gel of an immunoprecipitation of MSH2 from colorectal tumor cells using anti-MSH2 monoclonal antibody (mAb) FE11 and EH12.
Figure 2:
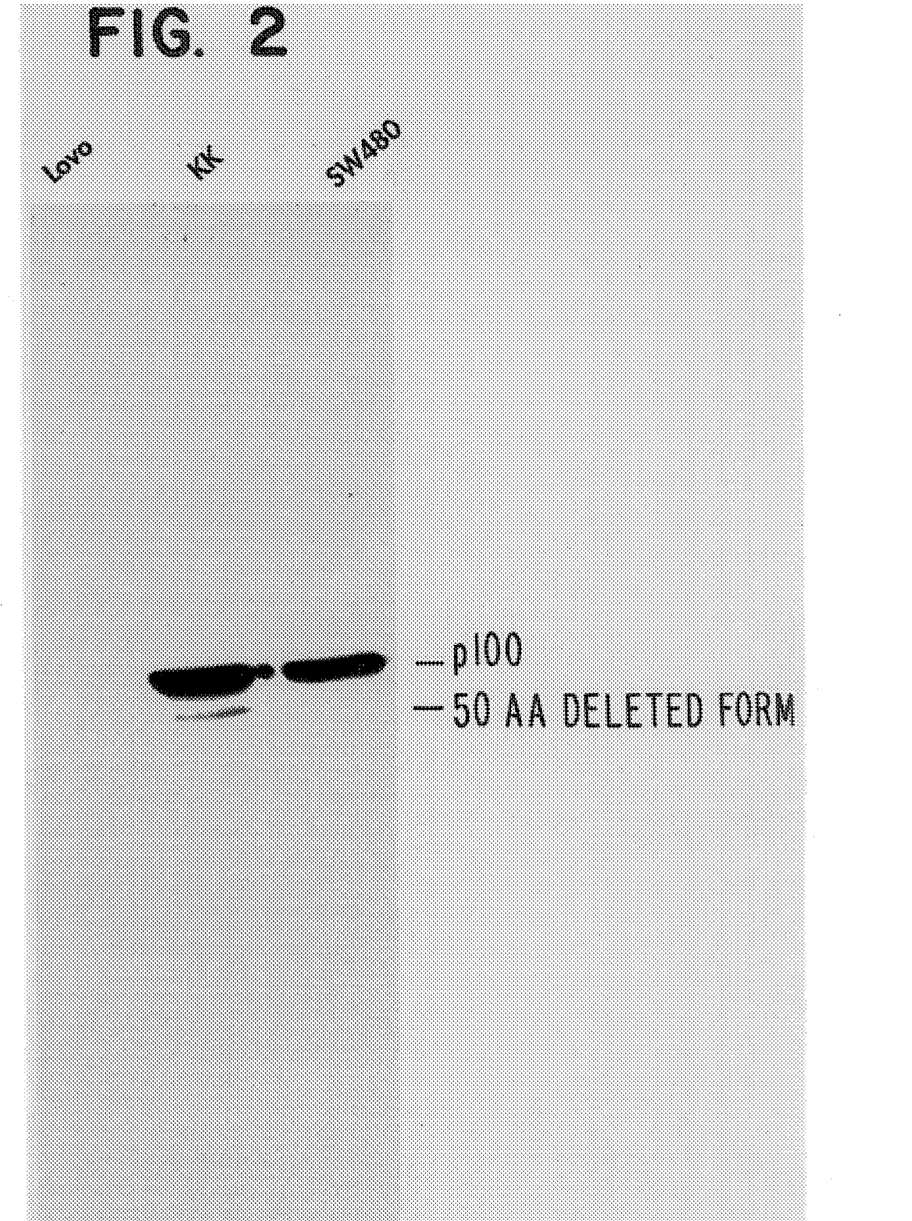
Figure 3A:
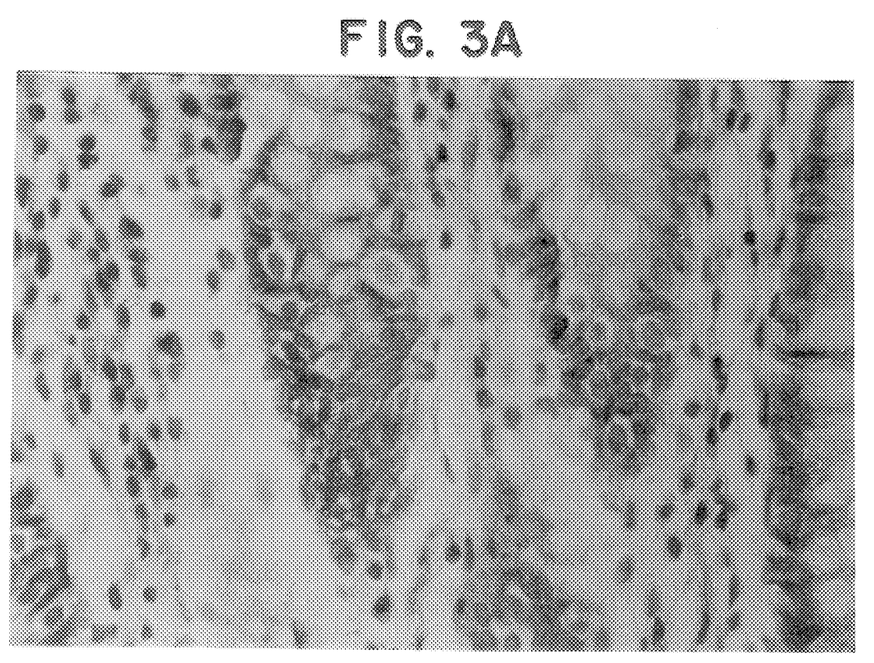
FIGS. 3A and 3B show immunohistochemical staining of MSH2 in normal colon with either FE11 or EH12.
Figure 3B:
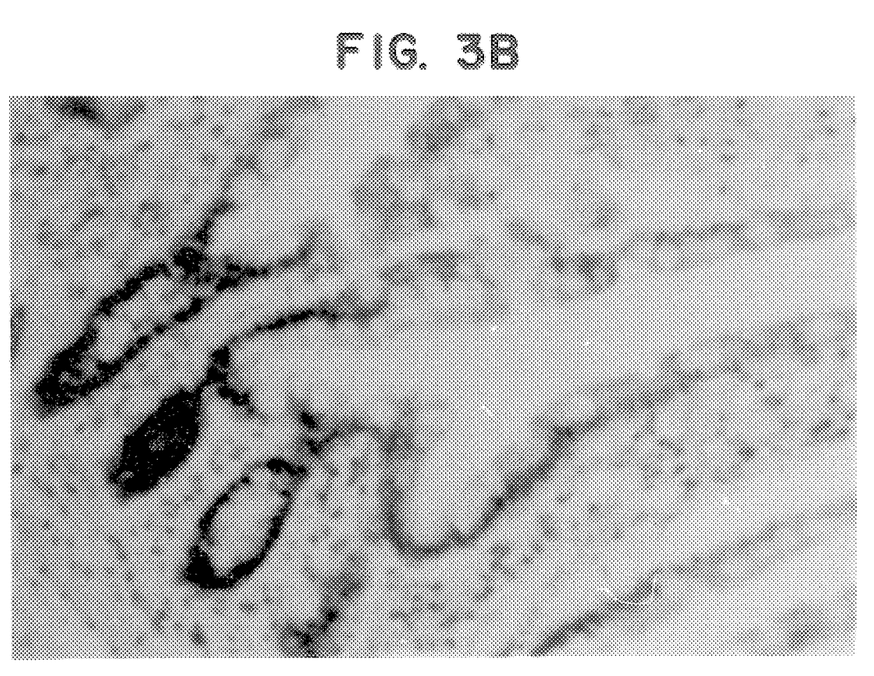

Since the DNA repair machinery involves at least four different gene products, we examined cell lysates for stable complexes of MSH2 and other proteins by immunoprecipitating, with either mAb FE11 or EH12, MSH2 from cells lysed under conditions that would preserve protein-protein interactions. Biochemical analysis of DNA mismatch repair in yeast had suggested that the yeast homolog of MSH2 is not ordinarily associated with other known DNA repair factors in the absence of mismatched DNA duplexes. FIG. 1 shows that in HCT 116 cells, which express wild-type MSH2, both antibodies immunoprecipitated a 160 kDa protein that is part of a co-precipitating complex with the 100 kDa MSH2 protein. This is not an alternative form of MSH2 or an MSH2 dimer since an immunoprecipitation with either FE11 or EH12 followed by immunoblotting with EH12 detects only the p100 MSH2 protein.

REFERENCES

Aaltonen, L. A., Peltomaki, P., Leach, F. S., Sistonen, P., Pylkkanen, L., Mecklin, J-P., Jarvinen, H., Powell, S. M., Jen, J., Hamilton, S. R., Petersen, G. M., Kinzler, K. W., Vogelstein, B., and de la Chapelle, A. (1993). Clues to the pathogenesis of familial colorectal cancer. Science 260, 812–816.

Fishel et al. (1993) The human mutator gene homolog MSH2 and its association with hereditary nonpolyposis colon cancer. Cell 75, 1927–1038.

Ionov, Y. M., Peinado, A., Malkhosyan, S., Shibata, D., and Perucho M. (1993). Ubiquitous somatic mutations in simple repeated sequences reveal a new mechanism for colonic carcinogenesis. Nature 363, 558–561.

Knudson, A. G. (1993). All in the (cancer) family. Nature Genetics 5, 103–104.

Kunkel, T. A. (1993). Slippery DNA and diseases. Nature 365, 207–208.

Leach et al. (1993) Mutations of a MutS Homolog in Hereditary Non-Polyposis Colorectal Cancer. Cell, 75, 1215–1225.

Lynch, H. T., Omaha, M. W., Shaw, M. D. (1966). Hereditary factors in cancer. Arch Intern Med 117, 206–212.

Lynch, H. T., Smyrk, T. C., Watson, P., Lanspa, S. J., Lynch, J. F., Lynch, P. M., Cavalieri, R. J., and Boland, C. R. (1993). Genetics, natural history, tumor spectrum, and pathology of hereditary nonpolyposis colorectal cancer: An updated review. Gastroenterology 104, 1535–1549.

Peinado, M. A., Malkhosyan, S., Velazquez, A., and Perucho, M. (1992). Isolation and characterization of allelic losses and gains in colorectal tumors by arbitrarily primed polymerase chain reaction. Proc. Natl. Acad. Sci. USA 89, 10065–10069.

Stanbridge, E. J. (1990). Human tumor suppressor genes. Ann. Rev. Genes 24, 615–657.

Strand, M., Prolla, T. A., Liskay, R. M., and Petes, T. D. (1993). Destabilization of tracts of simple repetitive DNA in yeast by mutations affecting DNA mismatch repair. Nature 365, 274–276.

Thibodeau, S. N., Bren, G., and Schaid, D. (1993). Microsatellite instability in cancer of the proximal colon. Science 260, 816–819.

Warthin, A. S. (1913). Heredity with reference to carcinoma: As shown by the study of the cases examined in the pathological laboratory of the University of Michigan, 1895–1913. Arch. Int. Med 12, 546–555.

We claim:

1. A method of discriminating proliferating from non-proliferating non-tumor colonic cells in a tissue, comprising the steps of:
   contacting a tissue comprising non-tumor colonic cells expressing only wild type forms of a mismatch repair protein selected from the group consisting of mismatch repair proteins consisting of hMSH2, hMLH1, and hPMS2 with antibodies specifically immunoreactive with the mismatch repair protein to form antibody-antigen complexes;
   determining the presence of said antibody-antigen complexes in said cells;
   identifying said cells as proliferating cells if they display said antibody-antigen complexes.

2. The method of claim 1 wherein the step of determining is by means of immunohistochemistry.

3. The method of claim 1 wherein the step of determining is by means of immunofluorescence.

4. The method of claim 1 wherein the step of determining is by means of fluorescence activated cell sorting.

5. The method of claim 1 wherein the mismatch repair protein is hMSH2.

6. The method of claim 1 wherein the mismatch repair protein is hMLH1.

7. The method of claim 1 wherein the mismatch repair protein is hPMS2.

8. A method of monitoring the effectiveness of anti-cancer therapy in neoplastic tissue, comprising the steps of:

contacting (1) a sample of a neoplastic tissue, wherein said tissue expresses only wild-type forms of mismatch repair protein hMSH2, and wherein said tissue has been subjected to an anti-cancer therapy, with (2) antibodies specifically immunoreactive with mismatch repair protein hMSH2, to form antibody-antigen complexes;

determining the amount of said antibody-antigen complexes in said sample;

comparing the amount of antibody-antigen complexes in said sample with an amount determined for the neoplastic tissue at an earlier time;

identifying the anti-cancer therapy as effective if a reduction in the amount of antibody-antigen complexes is observed.

9. The method of claim 8 wherein said step of determining is by immunohistochemistry.

10. The method of claim 8 wherein said step of determining is by immunofluorescence.

11. The method of claim 8 wherein said step of determining is by fluorescent activated cell sorting.

12. The method of claim 8 wherein said step of determining is by enzyme linked immunosorbent assay.

13. A method to discriminate proliferating from non-proliferating non-tumor colonic cells, comprising the steps of:

preparing a lysate of non-tumor colonic cells to be tested wherein said cells express only wild type forms of a mismatch repair protein selected form the group of mismatch repair proteins consisting of hMSH2, hMLH1, and hPMS2;

contacting said lysate with antibodies specifically immunoreactive with the mismatch repair protein, to form antibody-antigen complexes;

determining the amount of antibody-antigen complexes formed in said lysate;

identifying the test cells as proliferating cells if the lysate of test cells provides more antibody-antigen complexes than control lysates of non-tumor colonic cells.

14. The method of claim 13 wherein said step of determining is by means if enzyme linked immunosorbent assay.

15. The method of claim 13 wherein the mismatch repair protein is hMSH2.

16. The method of claim 13 wherein the mismatch repair protein is hMLH1.

17. The method of claim 13 wherein the mismatch repair protein is hPMS2.

18. A method to discriminate proliferating from nolproliferating non-tumor colonic cells, comprising the steps of:

isolating nuclei of test non-tumor colonic cells wherein said test cells express only wild type forms of a mismatch repair protein selected from the group of mismatch repair proteins consisting of hMSH2, hMLH1, and hPMS2;

preparing a lysate of said nucleic of said cells to be tested;

contacting said lysate with antibodies specifically immunoreactive with the mismatch repair protein, to form antibody-antigen complexes;

determining the amount of antibody-antigen complexes formed in said lysate;

identifying the test cells as proliferating if the lysate of nuclei provides more antibody-antigen complexes than control lysates of non-tumor colonic cell nuclei.

19. The method of claim 18 wherein said step of determining is performed by means of enzyme linked immunosorbent assay.

20. The method of claim 18 wherein the mismatch repair protein is hMSH2.

21. The method of claim 18 wherein the mismatch repair protein is hMLH1.

22. The method of claim 18 wherein the mismatch repair protein is hPMS2.

23. A method of discriminating proliferating from non-proliferating colonic cells in a tissue, comprising the steps of:

contacting a tissue comprising colonic cells expressing only wild type forms of mismatch repair protein hMSH2 with antibodies specifically immunoreactive with the mismatch repair protein to form antibody-antigen complexes;

determining the presence of said antibody-antigen complexes in said cells;

identifying said cells as proliferating cells if they display said antibody-antigen complexes.

24. A method to discriminate proliferating from non-proliferating colonic cells, comprising the steps of:

preparing a lysate of colonic cells to be tested wherein said cells express only wild type forms of mismatch repair protein hMSH2;

contacting said lysate with antibodies specifically immunoreactive with the mismatch repair protein, to form antibody-antigen complexes;

determining the amount of antibody-antigen complexes formed in said lysate;

identifying the test cells as proliferating cells if the lysate of test cells provides more antibody-antigen complexes than control lysates of non-tumor colonic cells.

25. A method to discriminate proliferating from non-proliferating colonic cells, comprising the steps of:

isolating nuclei of test colonic cells wherein said test cells express only wild type forms of mismatch repair protein hMSH2;

preparing a lysate of said nucleic of said cells to be tested;

contacting said lysate with antibodies specifically immunoreactive with the mismatch repair protein, to form antibody-antigen complexes;

determining the amount of antibody-antigen complexes formed in said lysate;

identifying the test colonic cells as proliferating if the lysate of nuclei provides more antibody-antigen complexes than control lysates of non-tumor colonic cell nuclei.

26. The method of claim 23 wherein the step of determining is by means of immunohistochemistry.

27. The method of claim 23 wherein the step of determining is by means of immunofluorescence.

28. The method of claim 23 wherein the step of determining is by means of fluorescence activated cell sorting.

29. The method of claim 24 wherein the step of determining is by means of enzyme linked immunosorbent assay.

30. The method of claim 24 wherein the step of determining is performed by means of enzyme linked immunosorbent assay.

* * * * *

UNITED STATES PATENT AND TRADEMARK OFFICE
CERTIFICATE OF CORRECTION

PATENT NO. : 6,048,701
DATED : April 11, 2000
INVENTOR(S) : Kenneth W. Kinzler, et al.

It is certified that error appears in the above-identified patent and that said Letters Patent is hereby corrected as shown below:

On the cover page, left column, below "OTHER PUBLICATIONS", the following has been inserted:

--Päivi Peltomäki, et al., "Genetic Mapping of a Locus Predisposing to Human Colorectal Cancer", Science, Vol. 260, 7 May 1993, pp. 810-812.

Lauri A. Aaltonen, et al., "Clues to the Pathogenesis of Familial Colorectal Cancer", Science, Vol. 260, 7 May 1993, pp. 812-816.

Rick Weise, "Gene for Colon Cancer Identified, Scientist Foresee Simple Blood Test for Heredity Forms of Disease", Washington Post, December 3, 1993, A1 and A24.

Burrell, et al., "Characterization of MSH2 Proteins in Sporadic and Inherited Forms of Colorectal Cancer", American Association for Cancer Research, Abstract presented at March 19, 1995 Meeting, Vol. 36, p. 194.

*Scc*-1, A Novel Colon Cancer Susceptibility Gene in the Mouse: Linkage to *CD44* (*Ly*-24, *Pgp*-1) on Chromosome 2, Corina J. A. Moen, et al., Oncogene (1992), 7, 563-566, MacMillian Press Ltd. 1992.

Ionov, et al., "Ubiquitous Somatic Mutations in Simple Repeated Sequences Reveal a New Mechanism for Colonic Carcinogenesis", Nature, 363:558-561, 1993.

Weissenbach, et al. "A Second-Generation Linkage Map of the Human Genome", Nature 359:794-801.

Weber, et al., " Abundant Class of Human DNA Polymorphisms Which Can Be Typed Using the Polymerase Chain Reaction", Am. J. Hum. Genet., 44:388-396 (1989).

Strand, et al., " Destabilization of Tracts of Simple Repetitive DNA in Yeast by Mutations Affecting DNA Mismatch Repair", Nature, 365:274-276 (1993). --

--Peltomäki, et al., "Evidence Supporting Exclusion of the *DCC* Gene and Portion of Chromosome 18q as the Locus for Susceptibility to Heredity Nonpolyposis Colorectal Carcinoma in Five Kindreds", Cancer Reseach 51:4135-4140 (1990).

UNITED STATES PATENT AND TRADEMARK OFFICE
CERTIFICATE OF CORRECTION

PATENT NO. : 6,048,701
DATED : April 11, 2000
INVENTOR(S) : Kenneth W. Kinzler, et al.

It is certified that error appears in the above-identified patent and that said Letters Patent is hereby corrected as shown below:

Peltomäki, et al., "Evidence that the *MCC-APC* Gene Region in 5q21 is Not the Site for Susceptibility to Hereditary Nonpolyposis Colorectal Carcinoma", Cancer Research 52:4530-4533 (1992).

Reenan, et al., Isolation and Characterization of the Two *Saccharomyces cerevisiae* Genes Encoding Homolgs of the Bacterial HexA and MutS Mismatch Repair Proteins", Genetics 132:963-973 (1992).

Haber, et al., "Nucleotide Sequence of the *Salmonella typhimurium mutS* Gene Required for Mismatch Repair: Homology of MutS and HexA of *Streptococcus pneumoniae*", J. Bacteriology 170(1):197-202 (1988).--

Claim 18, Column 23,
Lines 56 and 57, "nol-proliferating" has been deleted and in its place --non-proliferating-- has been inserted.

Claim 30, Column 24,
Line 63, "24" has been deleted and in its place --25-- has been inserted.

Signed and Sealed this

Nineteenth Day of June, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

```
    (i) SEQUENCE CHARACTERISTICS:
        (A) LENGTH: 934 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Homo sapiens (xi) SEQUENCE DESCRIPTION: SEQ ID NO:1:

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320
```

-continued

```
Thr Gly Ser Gln Ser Leu Ala Ala Leu Asn Lys Cys Lys Thr Pro
                325                 330                 335
Gln Gly Gln Arg Leu Val Asn Gln Trp Ile Lys Gln Pro Leu Met Asp
                340                 345                 350
Lys Asn Arg Ile Glu Glu Arg Leu Asn Leu Val Glu Ala Phe Val Glu
                355                 360                 365
Asp Ala Glu Leu Arg Gln Thr Leu Gln Glu Asp Leu Leu Arg Arg Phe
370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
                420                 425                 430
Leu Ala Val Phe Val Thr Pro Leu Thr Asp Leu Arg Ser Asp Phe Ser
                435                 440                 445
Lys Phe Gln Glu Met Ile Glu Thr Thr Leu Asp Met Asp Gln Val Glu
                450                 455                 460
Asn His Glu Phe Leu Val Lys Pro Ser Phe Asp Pro Asn Leu Ser Glu
465                 470                 475                 480
Leu Arg Glu Ile Met Asn Asp Leu Glu Lys Lys Met Gln Ser Thr Leu
                485                 490                 495
Ile Ser Ala Ala Arg Asp Leu Gly Leu Asp Pro Gly Lys Gln Ile Lys
                500                 505                 510
Leu Asp Ser Ser Ala Gln Phe Gly Tyr Tyr Phe Arg Val Thr Cys Lys
                515                 520                 525
Glu Glu Lys Val Leu Arg Asn Asn Lys Asn Phe Ser Thr Val Asp Ile
                530                 535                 540
Gln Lys Asn Gly Val Lys Phe Thr Asn Ser Lys Leu Thr Ser Leu Asn
545                 550                 555                 560
Glu Glu Tyr Thr Lys Asn Lys Thr Glu Tyr Glu Glu Ala Gln Asp Ala
                565                 570                 575
Ile Val Lys Glu Ile Val Asn Ile Ser Ser Gly Tyr Val Glu Pro Met
                580                 585                 590
Gln Thr Leu Asn Asp Val Leu Ala Gln Leu Asp Ala Val Val Ser Phe
                595                 600                 605
Ala His Val Ser Asn Gly Ala Pro Val Pro Tyr Val Arg Pro Ala Ile
                610                 615                 620
Leu Glu Lys Gly Gln Gly Arg Ile Ile Leu Lys Ala Ser Arg His Ala
625                 630                 635                 640
Cys Val Glu Val Gln Asp Glu Ile Ala Phe Ile Pro Asn Asp Val Tyr
                645                 650                 655
Phe Glu Lys Asp Lys Gln Met Phe His Ile Ile Thr Gly Pro Asn Met
                660                 665                 670
Gly Gly Lys Ser Thr Tyr Ile Arg Gln Thr Gly Val Ile Val Leu Met
                675                 680                 685
Ala Gln Ile Gly Cys Phe Val Pro Cys Glu Ser Ala Glu Val Ser Ile
                690                 695                 700
Val Asp Cys Ile Leu Ala Arg Val Gly Ala Gly Asp Ser Gln Leu Lys
705                 710                 715                 720
Gly Val Ser Thr Phe Met Ala Glu Met Leu Glu Thr Ala Ser Ile Leu
                725                 730                 735
```

```
Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
            755                 760                 765

Tyr Ile Ala Thr Lys Ile Gly Ala Phe Cys Met Phe Ala Thr His Phe
            770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
            805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
            835                 840                 845

Leu Glu Leu Glu Glu Phe Gln Tyr Ile Gly Glu Ser Gln Gly Tyr Asp
            850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
            885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
            915                 920                 925

Arg Ile Lys Val Thr Thr
930

(2) INFORMATION FOR SEQ ID NO:2:

(i) SEQUENCE CHARACTERISTICS:
        (A) LENGTH: 856 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
         (A) ORGANISM: Homo sapiens (xi) SEQUENCE DESCRIPTION: SEQ ID NO:2:

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
            50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
            85                  90                  95

Asp Leu Thr Gln Val Glu Thr Phe Gly Phe Arg Gly Glu Ala Leu Ser
            100                 105                 110
```

-continued

```
Ser Leu Cys Ala Leu Ser Asp Val Thr Ile Ser Thr Cys His Ala Ser
        115                 120                 125
Ala Lys Val Gly Thr Arg Leu Met Phe Asp His Asn Gly Lys Ile Ile
130                 135                 140
Gln Lys Thr Pro Tyr Pro Arg Pro Arg Gly Thr Thr Val Ser Val Gln
145                 150                 155                 160
Gln Leu Phe Ser Thr Leu Pro Val Arg His Lys Glu Phe Gln Arg Asn
                165                 170                 175
Ile Lys Lys Glu Tyr Ala Lys Met Val Gln Val Leu His Ala Tyr Cys
            180                 185                 190
Ile Ile Ser Ala Gly Ile Arg Val Ser Cys Thr Asn Gln Leu Gly Gln
        195                 200                 205
Gly Lys Arg Gln Pro Val Val Cys Thr Gly Gly Ser Pro Ser Ile Lys
210                 215                 220
Glu Asn Ile Gly Ser Val Phe Gly Gln Lys Gln Leu Gln Ser Leu Ile
225                 230                 235                 240
Pro Phe Val Gln Leu Pro Pro Ser Asp Ser Val Cys Glu Glu Tyr Gly
                245                 250                 255
Leu Ser Cys Ser Asp Ala Leu His Asn Leu Phe Tyr Ile Ser Gly Phe
            260                 265                 270
Ile Ser Gln Cys Thr His Gly Val Gly Arg Ser Ser Thr Asp Arg Gln
        275                 280                 285
Phe Phe Phe Ile Asn Arg Arg Pro Cys Asp Pro Ala Lys Val Cys Arg
    290                 295                 300
Leu Val Asn Glu Val Tyr His Met Tyr Asn Arg His Gln Tyr Pro Phe
305                 310                 315                 320
Val Val Leu Asn Ile Ser Val Asp Ser Glu Cys Val Asp Ile Asn Val
                325                 330                 335
Thr Pro Asp Lys Arg Gln Ile Leu Gln Glu Glu Lys Leu Leu Leu Leu
            340                 345                 350
Ala Val Leu Lys Thr Ser Leu Ile Gly Met Phe Asp Ser Asp Val Asn
        355                 360                 365
Lys Leu Asn Val Ser Gln Gln Pro Leu Leu Asp Val Glu Gly Asn Leu
370                 375                 380
Ile Lys Met His Ala Ala Asp Leu Glu Lys Pro Met Val Glu Lys Gln
385                 390                 395                 400
Asp Gln Ser Pro Ser Leu Arg Thr Gly Glu Glu Lys Lys Asp Val Ser
                405                 410                 415
Ile Ser Arg Leu Arg Glu Ala Phe Ser Leu Arg His Thr Thr Glu Asn
            420                 425                 430
Lys Pro His Ser Pro Lys Thr Pro Glu Pro Arg Arg Ser Pro Leu Gly
        435                 440                 445
Gln Lys Arg Gly Met Leu Ser Ser Ser Thr Ser Gly Ala Ile Ser Asp
    450                 455                 460
Lys Gly Val Leu Arg Pro Gln Lys Glu Ala Val Ser Ser Ser His Gly
465                 470                 475                 480
Pro Ser Asp Pro Thr Asp Arg Ala Glu Val Glu Lys Asp Ser Gly His
                485                 490                 495
Gly Ser Thr Ser Val Asp Ser Glu Gly Phe Ser Ile Pro Asp Thr Gly
            500                 505                 510
Ser His Cys Ser Ser Glu Tyr Ala Ala Ser Ser Pro Gly Asp Arg Gly
        515                 520                 525
```

-continued

```
Ser Gln Glu His Val Asp Ser Gln Lys Ala Pro Glu Thr Asp Asp
    530                 535                 540
Ser Phe Ser Asp Val Asp Cys His Ser Asn Gln Glu Asp Thr Gly Cys
545                 550                 555                 560
Lys Phe Arg Val Leu Pro Gln Pro Thr Asn Leu Ala Thr Pro Asn Thr
                565                 570                 575
Lys Arg Phe Lys Lys Glu Glu Ile Leu Ser Ser Ser Asp Ile Cys Gln
                580                 585                 590
Lys Leu Val Asn Thr Gln Asp Met Ser Ala Ser Gln Val Asp Val Ala
                595                 600                 605
Val Lys Ile Asn Lys Lys Val Val Pro Leu Asp Phe Ser Met Ser Ser
    610                 615                 620
Leu Ala Lys Arg Ile Lys Gln Leu His His Glu Ala Gln Gln Ser Glu
625                 630                 635                 640
Gly Glu Gln Asn Tyr Arg Lys Phe Arg Ala Lys Ile Cys Pro Gly Glu
                645                 650                 655
Asn Gln Ala Ala Glu Asp Glu Leu Arg Lys Glu Ile Ser Lys Thr Met
                660                 665                 670
Phe Ala Glu Met Glu Ile Ile Gly Gln Phe Asn Leu Gly Phe Ile Ile
                675                 680                 685
Thr Lys Leu Asn Glu Asp Ile Phe Ile Val Asp Gln His Ala Thr Asp
    690                 695                 700
Glu Lys Tyr Asn Phe Glu Met Leu Gln Gln His Thr Val Leu Gln Gly
705                 710                 715                 720
Gln Arg Leu Ile Ala Pro Gln Thr Leu Asn Leu Thr Ala Val Asn Glu
                725                 730                 735
Ala Val Leu Ile Glu Asn Leu Glu Ile Phe Arg Lys Asn Gly Phe Asp
                740                 745                 750
Phe Val Ile Asp Glu Asn Ala Pro Val Thr Glu Arg Ala Lys Leu Ile
                755                 760                 765
Ser Leu Pro Thr Ser Lys Asn Trp Thr Phe Gly Pro Gln Asp Val Asp
    770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                805                 810                 815
Met Ile Gly Thr Ala Leu Asn Thr Ser Glu Met Lys Lys Leu Ile Thr
                820                 825                 830
His Met Gly Glu Met Asp His Pro Trp Asn Cys Pro His Gly Arg Pro
                835                 840                 845
Thr Met Arg His Ile Ala Asn Leu
    850                 855
```

(2) INFORMATION FOR SEQ ID NO:3:

(i) SEQUENCE CHARACTERISTICS:
       (A) LENGTH: 752 amino acids
       (B) TYPE: amino acid
       (C) STRANDEDNESS: single
       (D) TOPOLOGY: linear (ii) MOLECULE TYPE: protein (iii) HYPOTHETICAL: YES (iv) ANTI-SENSE: NO (vi) ORIGINAL SOURCE:
    (A) ORGANISM: Homo sapiens (xi) SEQUENCE DESCRIPTION: SEQ ID NO:3:

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
            35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
    195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
    370                 375                 380

Arg Thr Asp Ser Arg Glu Gln Lys Leu Asp Ala Phe Leu Gln Pro Leu
385                 390                 395                 400

-continued

```
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
                420                 425                 430
Glu Leu Pro Ala Pro Ala Glu Val Ala Ala Lys Asn Gln Ser Leu Glu
                435                 440                 445
Gly Asp Thr Thr Lys Gly Thr Ser Glu Met Ser Glu Lys Arg Gly Pro
        450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
                500                 505                 510
Ile Asn Glu Gln Gly His Glu Val Leu Arg Glu Met Leu His Asn His
                515                 520                 525
Ser Phe Val Gly Cys Val Asn Pro Gln Trp Ala Leu Ala Gln His Gln
        530                 535                 540
Thr Lys Leu Tyr Leu Leu Asn Thr Thr Lys Leu Ser Glu Glu Leu Phe
545                 550                 555                 560
Tyr Gln Ile Leu Ile Tyr Asp Phe Ala Asn Phe Gly Val Leu Arg Leu
                565                 570                 575
Ser Glu Pro Ala Pro Leu Phe Asp Leu Ala Met Leu Ala Leu Asp Ser
                580                 585                 590
Pro Glu Ser Gly Trp Thr Glu Glu Asp Gly Pro Lys Glu Gly Leu Ala
        595                 600                 605
Glu Tyr Ile Val Glu Phe Leu Lys Lys Ala Glu Met Leu Ala Asp
        610                 615                 620
Tyr Phe Ser Leu Glu Ile Asp Glu Glu Gly Asn Leu Ile Gly Leu Pro
625                 630                 635                 640
Leu Leu Ile Asp Asn Tyr Val Pro Pro Leu Glu Gly Leu Pro Ile Phe
                645                 650                 655
Ile Leu Arg Leu Ala Thr Glu Val Asn Trp Asp Glu Glu Lys Glu Cys
                660                 665                 670
Phe Glu Ser Leu Ser Lys Glu Cys Ala Met Phe Tyr Ser Ile Arg Lys
            675                 680                 685
Gln Tyr Ile Ser Glu Glu Ser Thr Leu Ser Gly Gln Gln Ser Glu Val
        690                 695                 700
Pro Gly Ser Trp Lys Trp Thr Val Glu His Ile Val Tyr Lys Ala Leu
705                 710                 715                 720
Arg Ser His Ile Leu Pro Pro Lys His Phe Thr Glu Asp Gly Asn Ile
                725                 730                 735
Leu Gln Leu Ala Asn Leu Pro Asp Leu Tyr Lys Val Phe Glu Arg Cys
                740                 745                 750
```